US008343892B2

(12) United States Patent
Latorse et al.

(10) Patent No.: US 8,343,892 B2
(45) Date of Patent: Jan. 1, 2013

(54) FUNGICIDAL COMPOSITION COMPRISING A PYRIDYLMETHYLBENZAMIDE DERIVATIVE AND CHLOROTHALONIL

(75) Inventors: Marie-Pascale Latorse, Saint Romain de Popey (FR); Richard Mercer, Ecully (FR); Thomas Wegmann, Langenfeld (DE)

(73) Assignee: Bayer SAS (FR)

( * ) Notice: Subject to any disclaimer, the term of this patent is extended or adjusted under 35 U.S.C. 154(b) by 783 days.

(21) Appl. No.: 10/553,363

(22) PCT Filed: Apr. 14, 2004

(86) PCT No.: PCT/EP2004/004529
§ 371 (c)(1),
(2), (4) Date: Oct. 14, 2005

(87) PCT Pub. No.: WO2004/091299
PCT Pub. Date: Oct. 28, 2004

(65) Prior Publication Data
US 2006/0293369 A1    Dec. 28, 2006

(30) Foreign Application Priority Data
Apr. 15, 2003 (EP) .................................... 03356065

(51) Int. Cl.
*A01N 43/40* (2006.01)

(52) U.S. Cl. .......................................................... 504/130
(58) Field of Classification Search ................... 424/405
See application file for complete search history.

(56) References Cited

U.S. PATENT DOCUMENTS
6,503,933 B1 *  1/2003  Moloney et al. ............... 514/357

FOREIGN PATENT DOCUMENTS
| WO | WO 99/42447 | 8/1999 |
| WO | WO 02/069713 | 9/2002 |
| WO | WO 03/079788 | 10/2003 |

OTHER PUBLICATIONS

The Agrichemicals Handbook, A0090 / Aug. 1991.*
S.R. Colby, Calculating Synergistic and Antagonistic Responses of Herbicide Combinations, *Weeds*, (1967) 15, pp. 20-22.
P.M.L. Tammes, "Isoboles, A Graphic Representation of Synergism in Pesticides", *Netherlands Journal of Plant Pathology*, (1964) 70, pp. 73-80.

* cited by examiner

*Primary Examiner* — Alton Pryor
(74) *Attorney, Agent, or Firm* — Ostrolenk Faber LLP

(57) ABSTRACT

A fungicidal composition comprising at least a pyridylmethylbenzamide derivative of general formula (I) and a chloronitrile derivative which is chlorothalonil; in a compound (I)/chlorothalonil weight ratio of from 0.005 to 1. Method for preventively or curatively combating the phytopathogenic fungi of crops by using this composition.

4 Claims, No Drawings

FUNGICIDAL COMPOSITION COMPRISING A PYRIDYLMETHYLBENZAMIDE DERIVATIVE AND CHLOROTHALONIL

CROSS REFERENCE TO RELATED APPLICATION

The present application is a 35 U.S.C. §371 national phase conversion of PCT/EP2004/004529, filed Apr. 14, 2004, which claims priority of European Application No. 03356065.7 filed Apr. 15, 2003.

The present invention relates to novel fungicidal compositions comprising at least a pyridylmethylbenzamide derivative and a chloronitrile derivative. The present invention also relates to a method of combating phytopathogenic fungi by applying at a locus infested or liable to be infested such a composition.

European patent application EP-A-1056723 generically discloses the possibility of combining pyridylmethybenzamide derivatives with known fungicidal products to develop a fungicidal activity, without citing by name examples of co-active ingredients, or even families of co-active ingredients, which are capable of being combined with pyridylmethylbenzamide derivatives.

International patent application WO 02/069713 discloses fungicidal mixtures comprising a pyridylmethylbenzamide derivative and phosphorous acid or one of its derivatives. It is also disclosed that these combinations may also comprise additional fungicidal active materials, one of which may be chlorothalonil. See also U.S. Pat. No. 7,173,049.

Some of the above mentioned mixtures have shown a synergistic effect. Nevertheless, it is always of high-interest in agriculture to use novel pesticidal mixtures showing a synergistic effect in order to avoid or to control the development of resistant strains to the active ingredients or to the mixtures of known active ingredients used by the farmer while minimising the doses of chemical products spread in the environment and reducing the cost of the treatment.

We have now found some novel fungicidal compositions which possess the above mentioned characteristics.

Accordingly, the present invention relates to a fungicidal composition comprising:
a) a pyridylmethylbenzamide derivative of general formula (I)

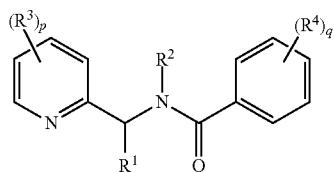

in which:
$R^1$ may be a hydrogen atom, an optionally substituted alkyl group or an optionally substituted acyl group;
$R^2$ may be a hydrogen atom or an optionally substituted alkyl group;
$R^3$ and $R^4$ may be chosen independently from each other as being a halogen atom, a hydroxyl group, a cyano group, a nitro group, —$SF_5$, a trialkylsilyl group, an optionally substituted amino group, an acyl group, or a group E, OE or SE, in which E may be an alkyl, alkenyl, alkynyl, cycloalkyl, cycloalkenyl, aryl or a heterocyclyl group each of which may optionally be substituted;

p represents 0, 1, 2, 3 or 4;
q represents 0, 1, 2, 3 or 4;
and its agriculturally acceptable optical and/or geometric isomers, tautomers and addition salts with an acid or a base; and
b) a chloronitrile derivative which is chlorothalonil;
in a compound (I)/chlorothalonil weight ratio of from 0.005 to 1.

Chlorothalonil is a fungicide compound also known under its chemical name which is tetrachloroisophthalonitrile.

In the context of the present invention:
the term halogen means bromine, chlorine, iodine or fluorine;
the term alkyl means a linear or branched saturated hydrocarbon group containing from 1 to 6 carbon atoms;
the term alkenyl means a linear or branched hydrocarbon group containing from 2 to 6 carbon atoms and an unsaturation in the form of double bond;
the term alkynyl means a linear or branched hydrocarbon group containing from 2 to 6 carbon atoms and an unsaturation in the form of a triple bond;
the term alkoxy means a linear or branched alkyloxy group containing from to 1 to 6 carbon atoms;
the term acyl means a formyl group or linear or branched alkoxycarbonyl group containing from 2 to 6 carbon atoms;
the term cycloalkyl means a saturated cyclic hydrocarbon group containing from 3 to 8 carbon atoms;
the term aryl means a phenyl or naphthyl group;
the term heterocyclyl means saturated, partially saturated, unsaturated or aromatic cyclic group containing from 3 to 8 atoms, which may be a carbon atom, a nitrogen atom, a sulphur atom or an oxygen atom. Examples of such heterocoyclyl may be pyridyl, pyridinyl, quinolyl, furyl, thienyl, pyrrolyl, oxazolinyl;
the term "optionally substituted" means that the group thus termed may be substituted with one or more groups which may be halogen, alkyl, alkoxy, hydroxyl, nitro, amin, cyano or acyl.

The composition according to the present invention provides a synergistic effect. This synergistic effect allows a reduction of the chemical substances spread into the environment and a reduction of the cost of the fungal treatment.

In the context of the present invention, the term "synergistic effect" is defined by Colby according to the article entitled "Calculation of the synergistic and antagonistic responses of herbicide combinations" Weeds, (1967), 15, pages 20-22.

The latter article mentions the formula:

$$E = x + y - \frac{x*y}{100}$$

in which E represents the expected percentage of inhibition of the disease for the combination of the two fungicides at defined doses (for example equal to x and y respectively), x is the percentage of inhibition observed for the disease by the compound (I) at a defined dose (equal to x), y is the percentage of inhibition observed for the disease by the compound (II) at a defined dose (equal to y). When the percentage of inhibition, observed for the combination is greater than E, there is a synergistic effect.

In the context of the present invention, the term "synergistic effect" also means the effect defined by application of the Tammes method, "Isoboles, a graphic representation of synergism in pesticides", Netherlands Journal of Plant Pathology, 70(1964), pages 73-80.

The fungicidal mixtures according to the present invention comprise a pyridylmethylbenzamide derivative of general formula (I).

Preferably, the present invention relates to a fungicidal mixture comprising a pyridylmethylbenzamide derivative of general formula (I) in which the different characteristics may be chosen alone or in combination as being:

as regards $R^1$ and $R^2$, $R^1$ and $R^2$ are chosen independently from each other as being a hydrogen atom or an optionally substituted alkyl group. More preferably, $R^1$ and $R^2$ are chosen independently from each other as being a hydrogen atom, a methyl group or an ethyl group. Even more preferably, $R^1$ and $R^2$ are both hydrogen atoms.

as regards $R^3$ and $R^4$, $R^3$ and $R^4$ are chosen independently from each other as being a halogen atom, a hydroxyl group, a nitro group, an optionally substituted amino group, an acyl group, or a group E, OE or SE, in which E may be a alkyl, a cycloalkyl, a phenyl or a heterocyclyl group, each of which may optionally be subtituted. More preferably, $R^3$ and $R^4$ are chosen independently from each other as being a halogen atom, a nitro group or a halogenoalkyl group. Even more preferably $R^3$ and $R^4$ are chosen independently from each other as being a chlorine atom, a nitro group or a trifluoromethyl group.

as regards p, p is 1 or 2. More preferably, p is 2.
as regards q, q is 1 or 2. More preferably, q is 2;
and its agriculturally acceptable possible tautomers and addition salts with an acid or a base.

More preferably, the present invention relates to a fungicidal mixture comprising a pyridylmethylbenzamide derivative of general formula (I) which may be chosen as being:

a compound (Ia) which is 2,6-dichloro-N-{[3-chloro-5-(trifluoromethyl)-2-pyridinyl]methyl}benzamide; or a compound (Ib) which is N-{[3-chloro-5-(trifluoromethyl)-2-pyridinyl]methyl}-2-fluoro-6-nitrobenzamide; or a compound (Ic) which is N-{[3-chloro-5-(trifluoromethyl)-2-pyridinyl]methyl}-2-methyl-6-nitrobenzamide; and its agriculturally acceptable possible tautomers and addition salts with an acid or a base.

The fungicidal mixture according to the present invention comprises a pyridylmethylbenzamide derivative of general formula (I) and chlorothalonil wherein the weight ratio of compound (I)/chlorothalonil is from 0.005 to 1; preferably from 0.01 to 0.5; more preferably, from 0.015 to 0.2.

A possible mixture according to the present invention may comprise a pyridylmethylbenzamide derivative of general formula (I) and chlorothalonil wherein the weight ratio of compound (I)/chlorothalonil is from 0.015 to less than 0.1; preferably from 0.015 to 0.0999; more preferably from 0.02 to 0.0999; even more preferably from 0.02 to 0.09.

A further possible mixture according to the present invention may comprise a pyridylmethylbenzamide derivative of general formula (I) and chlorothalonil wherein the weight ratio of compound (I)/chlorothalonil is from greater than 0.1 to 0.2; preferably from 0.1001 to 0.2; more preferably from 0.111 to 0.2; even more preferably from 0.12 to 0.2.

Following compositions may be cited to illustrate in a non-limited manner the present invention: compound (Ia) with chlorothalonil; compound (Ib) with chlorothalonil; compound (Ic) with chlorothalonil.

The present invention also relates to a fungicidal composition comprising at least one further active ingredient. Thus, according to the present invention, there is also provided a fungicidal composition as defined above which comprise at least one further fungicidal, herbicidal, insecticide and/or plant growth regulating compounds, according to the use for which they are intended.

The composition according to the present invention may further comprise an other additional component such as an agriculturally acceptable support, carrier or filler.

In the present specification, the term "support" denotes a natural or synthetic, organic or inorganic material with which the active material is combined to make it easier to apply, notably to the parts of the plant. This support is thus generally inert and should be agriculturally acceptable. The support may be a solid or a liquid. Examples of suitable supports include clays, natural or synthetic silicates, silica, resins, waxes, solid fertilisers, water, alcohols, in particular butanol, organic solvents, mineral and plant oils and derivatives thereof. Mixtures of such supports may also be used.

The composition may also comprise other additional components. In particular, the composition may further comprise a surfactant. The surfactant can be an emulsifier, a dispersing agent or a wetting agent of ionic or non-ionic type or a mixture of such surfactants. Mention may be made, for example, of polyacrylic acid salts, lignosulphonic acid salts, phenolsulphonic or naphthalenesulphonic acid salts, polycondensates of ethylene oxide with fatty alcohols or with fatty acids or with fatty amines, substituted phenols (in particular alkylphenols or arylphenols), salts of sulphosuccinic acid esters, taurine derivatives (in particular alkyl taurates), phosphoric esters of polyoxyethylated alcohols or phenols, fatty acid esters of polyols, and derivatives of the above compounds containing sulphate, sulphonate and phosphate functions; The presence of at least one surfactant is generally essential when the active material and/or the inert support are water-insoluble and when the vector agent for the application is water. Preferably, surfactant content may be comprised between 5% and 40% by weight of the composition.

Additional components may also be included, e.g. protective colloids, adhesives, thickeners, thixotropic agents, penetration agents, stabilisers, sequestering agents. More generally, the active materials can be combined with any solid or liquid additive, which complies with the usual formulation techniques.

In general, the composition according to the invention may contain from 0.05 to 99% (by weight) of active material, preferably 10 to 70% by weight.

Compositions according to the present invention can be used in various forms such as aerosol dispenser, capsule suspension, cold fogging concentrate, dustable powder, emulsifiable concentrate, emulsion oil in water, emulsion water in oil, encapsulated granule, fine granule, flowable concentrate for seed treatment, gas (under pressure), gas generating product, granule, hot fogging concentrate, macrogranule, microgranule, oil dispersible powder, oil miscible flowable concentrate, oil miscible liquid, paste, plant rodlet, powder for dry seed treatment, seed coated with a pesticide, soluble concentrate, soluble powder, solution for seed treatment, suspension concentrate (flowable concentrate), ultra low volume (ulv) liquid, ultra low volume (ulv) suspension, water dispersible granules or tablets, water dispersible powder for slurry treatment, water soluble granules or tablets, water soluble powder for seed treatment and wettable powder.

These compositions include not only compositions which are ready to be applied to the plant or seed to be treated by means of a suitable device, such as a spraying or dusting device, but also concentrated commercial compositions which must be diluted before they are applied to the crop.

The fungicidal compositions of the present invention can be used to curatively or preventively control the phytopathogenic fungi of crops. Thus, according to a further aspect of the present invention, there is provided a method for preventively or curatively controlling phytopathogenic fungi of crops characterised in that a fungicidal composition as hereinbefore defined is applied to the seed, the plant and/or to the fruit of the plant or to the soil in which the plant is growing or in which it is desired to grow.

The composition as used against phytopathogenic fungi of crops comprises an effective and non-phytotoxic amount of an active material of general formula (I).

The expression "effective and non-phytotoxic amount" means an amount of composition according to the invention which is sufficient to control or destroy the fungi present or liable to appear on the crops, and which does not entail any appreciable symptom of phytotoxicity for the said crops. Such an amount can vary within a wide range depending on the fungus to be combated, the type of crop, the climatic conditions and the compounds included in the fungicidal composition according to the invention.

This amount can be determined by systematic field trials, which are within the capabilities of a person skilled in the art.

The method of treatment according to the present invention is useful to treat propagation material such as tubers or rhizomes, but also seeds, seedlings or seedlings pricking out and plants or plants pricking out This method of treatment can also be useful to treat roots. The method of treatment according to the present invention can also be useful to treat the overground parts of the plant such as trunks, stems or stalks, leaves, flowers and fruits of the concerned plant.

Among the plants that can be protected by the method according to the invention, mention may be made of cotton; flax; vine; fruit or vegetables crops such as *Rosaceae* sp. (for instance pip fruits such as apples and pears, but also stone fruits such as apricots, almonds and peaches), *Ribesioldad* sp., *Juglandaceae* sp., *Betulaceae* sp., *Anacardiaceae* sp., *Fagaceae* sp., *Moraceae* sp., *Oleaceae* sp., *Actinidaceae* sp., *Lauraceae* sp., *Musaceae* sp. (for instance banana trees and plantins), *Rubiaceae* sp., *Theaceae* sp., *Sterculiceae* sp., *Rutaceae* sp. (for instance lemons, oranges and grapefruits); leguminous crops such as *Solanaceae* sp. (for instance tomatoes), *Liliaceae* sp., *Asteraceae* sp. (for instance lettuces), *Umbelliferae* sp., *Cruciferae* sp., *Chenopodiaceae* sp., *Cucurbitaceae* sp., *Papilionaceae* sp. (for instance peas), *Rosaceae* sp. (for instance strawberries); big crops such as *Graminae* sp. (for instance maize, lawn or cereals such as wheat, rice, barley and triticale), *Asteraceae* sp. (for instance sunflower), *Cruciferae* sp. (for instance, colza), *Papilionaceae* sp. (for instance soja), *Solanaceae* sp. (for instance potatoes), *Chenopodiaceae* sp. (for instance beetroots); horticultural and forest crops; as well as genetically modified homologues of these crops.

Among the plants and the possible diseases of these plants protected by the method according to the present invention, mention may be made of:

wheat, as regards controlling the following seed diseases: fisaria (*Microdochium nivale* and *Fusarium roseum*), stinking smut (*Tilletia caries, Tilletia controversa* or *Tilletia indica*), septoria disease (*Septoria nodorum*) and loose smut;

wheat, as regards controlling the following diseases of the aerial parts of the plant: cereal eyespot (*Tapesia yallundae, Tapesia acuiformis*), take-all (*Gaeumannomyces graminis*), foot blight (*F. culmorum, F. graminearum*), black speck (*Rhizoctonia cerealis*), powdery mildew (*Erysiphe graminis* forma specie *tritici*), rusts (*Puccinia striiformis* and *Puccinia recondita*) and septoria diseases (*Septoria tritici* and *Septoria nodorum*);

wheat and barley, as regards controlling bacterial and viral diseases, for example barley yellow mosaic;

barley, as regards controlling the following seed diseases: net blotch (*Pyrenophora graminea, Pyrenophora teres* and *Cochliobolus sativus*), loose smut (*Ustilago nuda*) and fusaria (*Microdochium nivale* and *Fusarium roseum*);

barley, as regards controlling the following diseases of the aerial parts of the plant: cereal eyespot (*Tapesia yallundae*), net blotch (*Pyrenophora teres* and *Cochliobolus sativus*), powdery mildew (*Erysiphe graminis* forma specie *hordei*), dwarf leaf rust (*Puccinia hordei*) and leaf blotch (*Rhynchosporium secalis*);

potato, as regards controlling tuber diseases (in particular *Helminthosporium solani, Phoma tuberosa, Rhizoctonia solani, Fusarium solani*), mildew (*Phytopthora infestans*) and certain viruses (virus Y);

potato, as regards controlling the following foliage diseases: early blight (*Alternaria solani*), mildew (*Phytophthora infestans*);

cotton, as regards controlling the following diseases of young plants grown from seeds: damping-off and collar rot (*Rhizoctonia solani, Fusarium oxysporum*) and black root rot (*Thielaviopsis basicola*);

protein yielding crops, for example peas, as regards controlling the following seed diseases: anthracnose (*Ascochyta pisi, Mycosphaerella pinodes*), fusaria (*Fusarium oxysporum*), grey mould (*Botrytis cinerea*) and mildew (*Peronospora pisi*);

oil-bearing crops, for example rape, as regards controlling the following seed diseases: *Phoma lingam, Alternaria brassicae* and *Scierotinia sclerotiorum;* corn, as regards controlling seed diseases: (*Rhizopus* sp., *Penicillium* sp., *Trichoderma* sp., *Aspergillus* sp., and *Gibberella fujikuroi*);

flax, as regards controlling the seed disease: *Alternaria linicola;* forest trees, as regards controlling damping-off (*Fusarium oxysporum, Rhizoctonia solani*);

rice, as regards controlling the following diseases of the aerial parts: blast disease (*Magnaporthe grisea*), bordered sheath spot (*Rhizoctonia solani*);

leguminous crops, as regards controlling the following diseases of seeds or of young plants grown from seeds: damping-off and collar rot (*Fusarium oxysporum, Fusarium roseum, Rhizoctonia solani, Pythium* sp.);

leguminous crops, as regards controlling the following diseases of the aerial parts: grey mould (*Botrytis* sp.), powdery mildews (in particular *Erysiphe cichoracearum, Sphaerotheca fuliginea* and *Leveillula taurica*), fusaria (*Fusarium oxysporum, Fusarium roseum*), leaf spot (*Cladosporium* sp.), alternaria leaf spot (*Alternaria* sp.), anthracnose (*Colletotrichum* sp.), septoria leaf spot (*Septoria* sp.), black speck (*Rhizoctonia solani*), mildews (for example *Bremia lactucae, Peronospora* sp., *Pseudoperonospora* sp., *Phytophthora* sp.);

fruit trees, as regards diseases of the aerial parts: monilia disease (*Monilia fructigenae, M. laxa*), scab (*Venturia inaequalis*), powdery mildew (*Podosphaera leucotricha*);

vine, as regards diseases of the foliage: in particular grey mould (*Botrytis cinerea*), powdery mildew (*Uncinula necator*), black rot (*Guignardia biwelli*) and mildew (*Plasmopara viticola*);

beetroot, as regards the following diseases of the aerial parts: cercospora blight (*Cercospora beticola*), powdery mildew (*Erysiphe beticola*), leaf spot (*Ramularia beticola*).

Preferably, the plant that can be protected by the method according to the present invention is potato, vegetables or lawn.

The fungicide composition according to the present invention may also be used against fungal diseases liable to grow on or inside timber. The term "timber" means all types of species of wood, and all types of working of this wood intended for construction, for example solid wood, high-density wood, laminated wood, and plywood. The method for treating timber according to the invention mainly consists in contacting one or more compounds of the present invention, or a composition according to the invention; this includes for example direct application, spraying, dipping, injection or any other suitable means.

The dose of active material usually applied in the treatment according to the present invention is generally and advantageously between 10 and 1500 g/ha, preferably between 50 and 1000 g/ha for applications in foliar treatment. The dose of active substance applied is generally and advantageously between 2 and 200 g per 100 kg of seed, preferably between 3 and 15 g per 100 kg of seed in the case of seed treatment. It is clearly understood that the doses indicated above are given as illustrative examples of the invention. A person skilled in the art will know how to adapt the application doses according to the nature of the crop to be treated.

The fungicidal composition according to the present invention may also be used in the treatment of genetically modified organisms with the compounds according to the invention or the agrochemical compositions according to the invention. Genetically modified plants are plants into whose genome a heterologous gene encoding a protein of interest has been stably integrated. The expression "heterologous gene encoding a protein of interest" essentially means genes which give the transformed plant new agronomic properties, or genes for improving the agronomic quality of the transformed plant.

The compositions according to the present invention may also be used for the preparation of composition useful to curatively or preventively treat human and animal fungal diseases such as, for example, mycoses, dermatoses, trichophyton diseases and candidiases or diseases caused by *Aspergillus* spp., for example *Aspergillus fumigatus*.

The present invention will now be illustrated by way of the following examples.

EXAMPLE 1

Treatment of Tomato with a Composition According to the Invention

This example demonstrates a synergy for a mixture of 2,6-dichloro-N-{[3-chloro-5-(trifluoromethyl)-2-pyridinyl] methyl}benzamide (compound Ia) and chlorothalonil on Late blight (*Phytophthora infestans*) in 48 h preventive application on tomato.

Tomato seedlings (Marmande variety) were grown in a compost soil in plastic pots with a single plant per pot. At the age of 1 months, these plants were sprayed with the two fungicide compounds either alone or in a mixture. Fungicide compounds applied in mixtures were also applied singly at the same doses as those used in the combinations. The fungicide compounds, either alone or in mixtures, were applied at a volume rate of 300 l water per ha.

Six weight ratios of the mixture of compound Ia/chlorothalonil have been studied: 1/1; 1/2; 1/5; 1/7.5 and 1/20.

Starting with compound Ia in the form of suspension concentrate (SC) at 480 g/l and chlorothalonil in the form of SC at 500 g/l (Fungistop), plant protection mixtures for application corresponding to a volume of 300 l of liquid per ha are prepared.

The dose range of compound Ia corresponds to 100 mg/l, 75 mg/l, 50 mg/l, 16 mg/l, 10 mg/l, 8 mg/l, 5 mg/l, 2 mg/l and 1 mg/l.

Two days after treatment, each plant was inoculated by spraying an aqueous suspension of sporangia of *Phytophthora infestans* obtained from contaminated leaves. The concentration of sporangia was about 10,000 units per ml.

After contamination the plants were incubated for 5 days at 16° C. in a saturated atmosphere.

Five days after contamination, symptoms were evaluated in terms of the extent of the lower surface of the leaves infected, in comparison with untreated but contaminated plants.

The efficacy of the treatment was calculated using the Abbott formula:

Efficacy=(Untreated−Treated/Untreated)×100

The concentrations of the fungicide compounds alone or in a mixture giving 70% and 90% efficacy for each component were determined based on the sigmoid curve dose/response model with their confidence intervals.

The analyses of the results were carried out using the TAMMES model (Isoboles, a graphic representation of synergism in pesticides, Neth. J. Plant Path. 70 (1964): 73-80) or Colby model.

The results obtained are presented in the form of point values, corresponding to 70% or 90% control of the pathogen and placed in a Tammes isobole diagram which comprises on the x-axis the doses of Compound Ia expressed in mg/l and on the y-axis the doses of chlorothalonil also in mg/l.

The calculated results corresponding to ED70 and ED90 (effective doses providing 70% and 90% of disease control) for the various ratios of the mixtures that have been evaluated are presented in the following Table 1 and Table 2.

TABLE 1

| | ED70 | | | | | |
|---|---|---|---|---|---|---|
| | Compound Ia: chlorothalonil ratio | | | | Compound | Chloro- thalonil |
| | 1:1 | 1:2 | 1:7.5 | 1:20 | Ia alone | alone |
| Practical doses for 70% efficacy (in mg/l) | 3.2 3.2 | 3.2 6.4 | 1.4 10.5 | 0.4 8 | 52.3 | 16.1 |
| Theoretical dose for 70% efficacy (in lg/l) | 12.5 12.5 | 7 14 | 2 15 | 0.8 16 | — | — |

TABLE 2

| | ED90 | | | | | |
|---|---|---|---|---|---|---|
| | Compound Ia: chlorothalonil ratio | | | | Compound | Chloro- thalonil |
| | 1:1 | 1:2 | 1:7.5 | 1:20 | Ia alone | alone |
| Practical doses for 90% efficacy (in mg/l) | 8.7 8.7 | 8.7 17.4 | 2.8 10.5 | 1 20 | 181 | 36.7 |
| Theoretical dose for 90% efficacy (in mg/l) | 30.5 30.5 | 16.5 33 | 4.6 35 | 1.8 36.5 | | |

These results have been calculated on the basis of 3 repeats per factor according to the Tammes method taking into account the product efficacy for a range of ratios and for method for 70% and 90% of disease control on tomato.

This preventive test on tomato late blight shows the synergism of the fungicide compositions containing compounds A and B at ratios equal to 1/1, 1/2, 1/7.5 and 1/20. It has been demonstrated that less amount of both compounds are necessary to control 70% and 90% of the disease compared to the theoretical doses of each compounds expected in the mixture with just additional effect.

A synergy of the above mixture is also demonstrated when data are analysed according to Colby method. Following Table 3 presents the results obtained based on using the Colby method for evaluating the synergy of the mixture of compound Ia with chlorothalonil according to the invention. Practical efficacy is superior to theoretical efficacy showing the synergism of the fungicide compositions containing compounds Ia and chlorothalonil at ratios equal to 1/2, 1/5, 1/7.5 and 1/20.

TABLE 3

Synergism according Colby method between compound Ia and chlorothalonil on tomato late blight

| Dose of compound Ia (mg/l) + | 10 | 5 | 1 | 5 | 5 | 5 | 1 |
|---|---|---|---|---|---|---|---|
| Dose of chlorothalonil (mg/l) | 10 | 5 | 7.5 | 37.5 | 10 | 25 | 20 |
| Practical efficacy % | 89 | 83 | 54 | 97 | 83 | 78 | 92 |
| Theoretical efficacy % | 66 | 38 | 38 | 94 | 55 | 71 | 87 |

EXAMPLE 2

Treatment of Potato Foliar Disc with a Composition According to the Invention

This example demonstrates a synergy for a mixture of 2,6-dichloro-N-{[3-chloro-5-(trifluoromethyl)-2-pyridinyl]methyl}benzamide (compound Ia) and chlorothalonil on Late blight (*Phytophthora infestans*) in 24 h preventive application on potato.

This test was conducted on potato foliar disc. Potato plants (Bintje variety), were grown in a sandy loam soil in plastic pots with a single plant per pot. When the potatoes were one and a half months old, foliar discs were collected and put on survival agar medium complemented with 2 mg/l of kinetine in Petri dishes (30 foliar discs per rate in 3 Petri dishes).

They were sprayed with the two fungicide compounds either alone or in a mixture. Fungicide compounds applied in mixtures were also applied singly at the same doses as those used in the combinations. The fungicide compounds, either alone or in mixtures, were applied at a volume rate of 300 l water per ha.

Six weight ratios of the mixture of compound Ia/chlorothalonil have been studied: 1/1; 1/2; 1/5; 1/7.5 and 1/20.

Starting with compound Ia in the form of suspension concentrate (SC) at 480 g/l and chlorothalonil in the form of SC at 500 g/l (Fungistop), plant protection mixtures for application corresponding to a volume of 300 l of liquid per ha are prepared.

One day after treatment, the inoculation was done by deposit of a 10 µl droplet of sporangial suspension of *Phytophthora infestans* (40 000 spores/ml) on the adaxial face of each disc.

Petri dishes were incubated under controlled conditions (16° C., RH 90%, 16 h/8 h light/dark).

6 days after contamination, symptoms were assessed based on the surface area of the foliar disc infected, in comparison with untreated but contaminated foliar discs.

The results obtained are summarized in the following Table. Practical efficacy is superior to theoretical efficacy showing the synergism of the fungicide compositions containing compounds Ia and chlorothalonil at ratios equal to 1/2, 1/5, 1/7.5 and 1/20.

TABLE 4

Synergism according Colby method between compound Ia and chlorothalonil on potato late blight

| Dose of compound Ia (mg/l) + | 2 | 1 | 2 | 2 | 1 |
|---|---|---|---|---|---|
| Dose of chlorothalonil (mg/l) | 4 | 5 | 10 | 15 | 20 |
| Practical efficacy % | 59 | 25 | 55 | 55 | 27 |
| Theoretical efficacy % | 31 | 2 | 31 | 31 | 21 |

The invention claimed is:

1. A method for preventively controlling *Phytophthora infestans* in plants selected
   from the group consisting of potatoes and tomatoes comprising applying to the plant and/or the
   fruit of the plant an effective and non-phytotoxic amount of a composition comprising:
   (a) 2,6-dichloro-N-{[3-chloro-5-(trifluoromethyl)-2-pyridinyl]methyl}benzamide, also known as fluopicolide; and
   (b) chlorothalonil;
   in a fluopicolide/chlorothalonil weight ratio of from 1:2 to 1:1, inclusive.

2. The method of claim 1 wherein the plant is tomato.

3. The method of claim 1 wherein the composition further comprises a member selected from the group consisting of an agriculturally acceptable support, a carrier, a filler, and a surfactant.

4. The method of claim 2 wherein the composition further comprises a member selected from the group consisting of an agriculturally acceptable support, a carrier, a filler, and a surfactant.

* * * * *